(12) United States Patent
Mussack et al.

(10) Patent No.: US 7,496,222 B2
(45) Date of Patent: Feb. 24, 2009

(54) METHOD TO DEFINE THE 3D OBLIQUE CROSS-SECTION OF ANATOMY AT A SPECIFIC ANGLE AND BE ABLE TO EASILY MODIFY MULTIPLE ANGLES OF DISPLAY SIMULTANEOUSLY

(75) Inventors: Christopher Joseph Mussack, Waukesha, WI (US); Litao Yan, Waukesha, WI (US); Cheryl Ruth Jones, Hubertus, WI (US); David Charles Mack, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 644 days.

(21) Appl. No.: 11/202,777

(22) Filed: Aug. 12, 2005

(65) Prior Publication Data
US 2006/0291717 A1    Dec. 28, 2006

Related U.S. Application Data

(60) Provisional application No. 60/695,327, filed on Jun. 23, 2005.

(51) Int. Cl.
G06K 9/00 (2006.01)
G06F 17/00 (2006.01)
G06T 1/00 (2006.01)
(52) U.S. Cl. .................................. 382/131; 345/418
(58) Field of Classification Search ................ 382/131; 345/419, 424, 427, 440
See application file for complete search history.

(56) References Cited
U.S. PATENT DOCUMENTS 5,371,778 A * 12/1994 Yanof et al. ............... 378/4
5,734,384 A * 3/1998 Yanof et al. ............... 345/424
5,986,662 A * 11/1999 Argiro et al. .............. 345/424
6,603,868 B1 * 8/2003 Ludwig et al. ............ 382/128
6,801,643 B2 * 10/2004 Pieper ..................... 382/128
7,061,484 B2 * 6/2006 Bailey et al. .............. 345/419

(Continued)

OTHER PUBLICATIONS

*Advanced Clinical Application Training for 3D Imaging & Virtual Colonoscopy*, University of Florida Health Science Center Jacksonville Brochure (2004).

(Continued)

*Primary Examiner*—Samir A. Ahmed
*Assistant Examiner*—Li Liu
(74) *Attorney, Agent, or Firm*—McAndrews, Held & Malloy, Ltd.; Peter J. Vogel; Michael A. Dellapenna (57) ABSTRACT

The present invention provides a system and a method for simultaneously modifying one or more angles of cross-sections in one or more cross-sectional images or stacks of images of a 3D volume. A plurality of viewports is displayed to a user. Each viewport includes a 2D cross-sectional image or stack of images and all 2D images or stacks of images are displayed simultaneously. One or more viewports may also include a control line representative of an angle of cross-section or image plane of a 2D image or stack of images displayed in another viewport. If a control line is moved in a selected viewport, the angle of cross-section or image plane of a 2D image or stack of images in another viewport is accordingly altered simultaneous with such control line movement.

15 Claims, 6 Drawing Sheets

U.S. PATENT DOCUMENTS 7,315,304 B2 * 1/2008 Liang et al. .................. 345/426

OTHER PUBLICATIONS

*Aquarius Blue Simple to Use 2D, 3D Tool for Every Workflow*, TeraRecon, Inc. Brochure.

*Aquarius Net Enterprise Wide Interactive 3D Image Distribution*, TeraRecon, Inc. Brochure.

*Vital Images Inc.* website, Retrieved Aug. 11, 2005, www.vitalimages.com.

*Aquarius Premier 2D/3D/4D Imaging Workstation*, TeraRecon, Inc. Brochure.

*TeraRecon, Inc.—Aquarius Workstation and AquariusNet Server for Cardiac & Vascular CT and MR*, TeraRecon, Inc. Brochure.

* cited by examiner

METHOD TO DEFINE THE 3D OBLIQUE CROSS-SECTION OF ANATOMY AT A SPECIFIC ANGLE AND BE ABLE TO EASILY MODIFY MULTIPLE ANGLES OF DISPLAY SIMULTANEOUSLY

RELATED APPLICATIONS

This application claims the benefit of U.S. Provisional Application No. 60/695,327, filed Jun. 23, 2005, entitled "A Method to Define the 3D Oblique Cross-Section of Anatomy at a Specific Angle and be Able to Easily Modify Multiple Angles of Display Simultaneously." The disclosure of the '327 application is hereby incorporated by reference in its entirety.

FEDERALLY SPONSORED RESEARCH OR DEVELOPMENT

Not applicable.

BACKGROUND OF THE INVENTION

The present invention generally relates to the viewing of medical images at several angles. More specifically, the present invention relates to defining a three-dimensional ("3D") oblique cross-section of an anatomy at a specific angle and to modify additional angles of display simultaneously.

Current systems and methods allow for the viewing of a 3D volume of an object, such as a patient's anatomy, in one or more two-dimensional ("2D") cross-sectional images or cross-sectional stack of images of the 3D volume. The angle of display in the 2D cross-sectional images may be manipulated by a user.

The angle of display in the 2D images may be manipulated or adjusted by rotating the image about a line (such as a control line, for example) displayed on a 2D image. In general, movement of a control line in a first 2D image can affect the angle of display of a 2D image in another, subsequently viewed 2D image. For example, current systems may display a control line over a first 2D cross-sectional image. This control line can represent a 2D image plane in which a view of the 3D image is presented in a subsequent 2D image. By moving the control line in the first 2D image, the 2D image plane (and consequently the 2D image representation of the 3D image) in the second 2D image will change when the second 2D image is viewed. Moreover, current systems permit the user to then move a control line in the second 2D image to adjust the 2D image plane of the next subsequent 2D image. The movement of a control line in one 2D image affects the angle of display or 2D image plane in all subsequent 2D images. Moreover, when a control line in a first 2D image is moved, the angles of display or image planes in all subsequent 2D images are adjusted. In other words, changing the angle of display in a first 2D image has a domino effect of changing the angle of display in all subsequent 2D images.

The movement of control lines so as to adjust angles of display in multiple 2D images is used to obtain a final 2D image that is positioned correctly according to a user's needs. By moving control lines in one or more 2D images so as to affect the angles of display or the angle of the cross-section in subsequent 2D images (including the final 2D image), a user is able to obtain a preferred angle of display in the final 2D image.

However, while current systems may display more than a single 2D image at a time, these systems typically display only a single step of the double oblique process. That is, current systems display one image with a control line, and another image with the result(s) of moving that control line. Current systems do not include multiple control lines in multiple images, thereby prohibiting the display of multiple steps of the double oblique process. Therefore, users are unable to move multiple control lines in multiple 2D images and are therefore unable to witness multiple steps of the double oblique process simultaneously.

Thus, current systems and methods do not allow the easy manipulation of the angle of display or the angle of cross-section in multiple cross-sectional images or cross-sectional stacks of images of a 3D volume in multiple viewports or displays. For example, when attempting to view a specific portion of an anatomy in a medical image in 3D Maximum Intensity Pixel ("MIP")/Multi-Planar Reformat ("MPR") mode, free rotation, or rotation about a single line cannot always position the desired anatomy correctly in one or more of the subsequent viewports. In other words, a user of a software application attempting to view a portion of an anatomy in a particular position may need to position the anatomical portion using multiple rotations about several lines in multiple viewports.

For example, when attempting to obtain a view through a spinal disk on a patient with scoliosis (curved spine), the user would need to complete a two-step cross-sectioning process using existing methods:
 1. Prescribe a pseudo-sagittal view by defining a line along the spine on a coronal view.
 2. Prescribe a view straight through the disk by defining a line on the pseudo sagittal view.

As described above, a major drawback of the existing methods is that the user can only see one prescribed cross-sectional view at a time. This implies that while the user is looking at the final view he can no longer see the coronal view; likewise, while performing the first step the user cannot see the final view. As a result, if the user cannot obtain the view through the disk correctly, the user may need to go back to the first step to adjust the pseudo-sagittal view from the coronal image. However, the user will no longer be able to see if the adjustments made are correct on the final image. This will typically result in multiple iterations before a correct view through the disk can be obtained.

The above example shows that the existing oblique cross-sectioning methods are oftentimes time-consuming when used to obtain a view through multiple cross-sections. Therefore, a need exists for a more efficient method for obtaining a view through multiple cross-sections of an image.

BRIEF SUMMARY OF THE INVENTION

The present invention provides a method to modify one or more angles of cross-section in one or more cross-sectional images of a 3D volume simultaneously. The method includes providing a plurality of viewports, where each of the viewports is configured to display one or more 2D images, moving a control line in a selected viewport, and altering an angle of cross-section of at least one of the 2D images in at least one viewport other than the selected viewport simultaneous with the step of moving the control line. The 2D images can represent one or more cross-sections of the 3D volume.

The present invention also provides a computer-readable storage medium including a set of instructions for a computer. The set of instructions includes a display routine and an angle of cross-section modifying routine. The display routine is configured to display a 2D image representative of a cross-section of a 3D volume in each of a plurality of viewports. The modifying routine is configured to alter an angle of cross-section of at least one of the 2D images based on and simultaneous with a movement of a control line in a selected viewport.

The present invention also provides a method for adjusting an angle of cross-section in at least one of a plurality of 2D images. The method includes providing a plurality of viewports including first, second and final viewports, displaying a plurality of control lines including first and second control lines, moving the first control line, and adjusting a first angle of display of a second 2D image and a second angle of display of a final 2D image simultaneous with moving the first control line. The first, second and final viewports are configured to display first, second and final 2D images, respectively. The first, second and final 2D images each representative of one or more cross-sections of a 3D volume. The first control line is displayed in the first viewport and the second control line is displayed in the second viewport. The first control line is configured to represent cross-sectional plane of the second 2D image at a first angle of cross-section and the second control line is configured to represent a cross-sectional plane of the final 2D image at a second angle of cross-section.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 5:
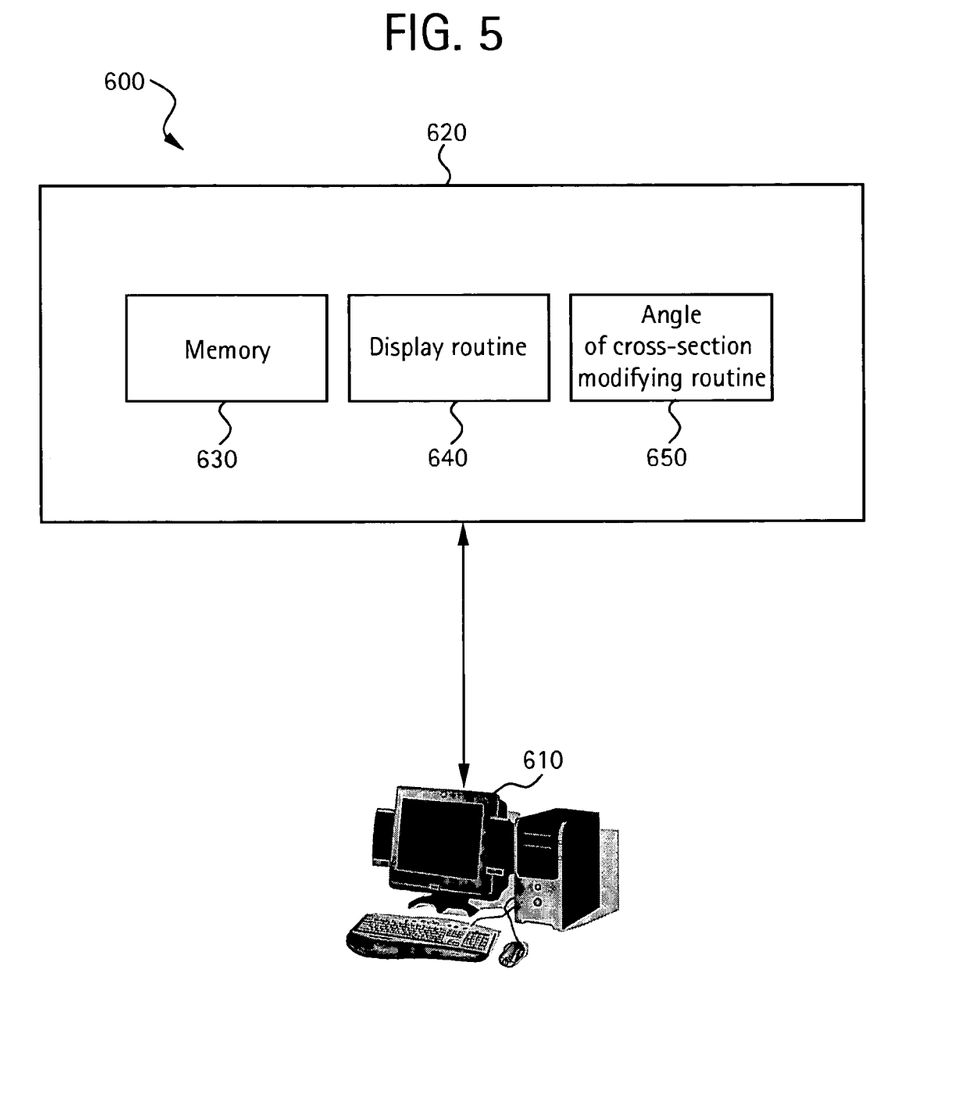
FIG. 5 illustrates a system for simultaneously modifying one or more angles of display or angles of cross-section in one or more cross-sectional images or cross-sectional stack of images of a 3D volume according to an embodiment of the present invention.

FIG. 5 illustrates a system 600 for simultaneously modifying one or more angles of display or angles of cross-section in one or more cross-sectional images or cross-sectional stack of images of a 3D volume according to an embodiment of the present invention. System 600 includes a computing device 610 and a computer-readable storage medium 620. Computing device 610 may include any one or more interconnected machines capable of carrying out operations based on one or more set of instructions. While a personal computer is shown as device 610 in FIG. 5, the various embodiments of the present invention are not limited to a personal computer. Any one or more interconnected machines capable of carrying out operations based on one or more set of instructions may comprise device 610. A set of instructions may include, for example, a software application or program, for example. Medium 620 may include any computer-readable storage medium, such as a local and/or remote memory. For example, medium 620 may include a computer hard drive (internal or external) or a memory in a server accessible via a network connection.

Medium 620 includes a memory 630 and one or more sets of instructions including a display routine 640 and an angle of cross-section modifying routine 650. Memory 630 may include any portion of medium 620 dedicated to the storage of one or more sets of instructions (for example, software applications), imaging studies, and/or images. Display routine 640 may include any set(s) of instruction(s) capable of directing computing device 610 to carry out one or more tasks. Similarly, modifying routine 650 may include one or more set(s) of instruction(s) capable of directing computing device 610 to carry out one or more tasks. As understood by one of ordinary skill in the art, display routine 640 and modifying routine 650 may be written and carried out in any suitable computer-programming language. Display routine 640 and/or modifying routine 650 may be implemented locally (that is, put into operation by a processor of computer or workstation) or remotely (that is, put into operation by a processor of a remote computer, workstation or server), for example.

A user may employ system 600 to view a plurality of 2D cross-sectional images or cross-sectional stack of images of a 3D volume. In accordance with an embodiment of the present invention, at least one technical effect of display routine 640 and modifying routine 650 is to permit a user to simultaneously modify one or more angles of display or angles of cross-section in one or more cross-sectional images or stacks of images of a 3D volume. For example, a user may access one or more images and/or imaging studies of a patient anatomy using device 610. The images and/or imaging studies may be stored locally on a memory 630 in device 610 or in a memory 630 remote from device 610 and accessible via one or more network connections, for example.

A user may load or run a software application to examine the image(s) and/or imaging study(ies) on device 610. In an embodiment of the present invention, device 610 loads display routine 640 to display one or more 2D images. The 2D image(s) may be presented in one or more viewports. A viewport may include a subscreen or subdivision of a display screen of device 610.

Figure 1:
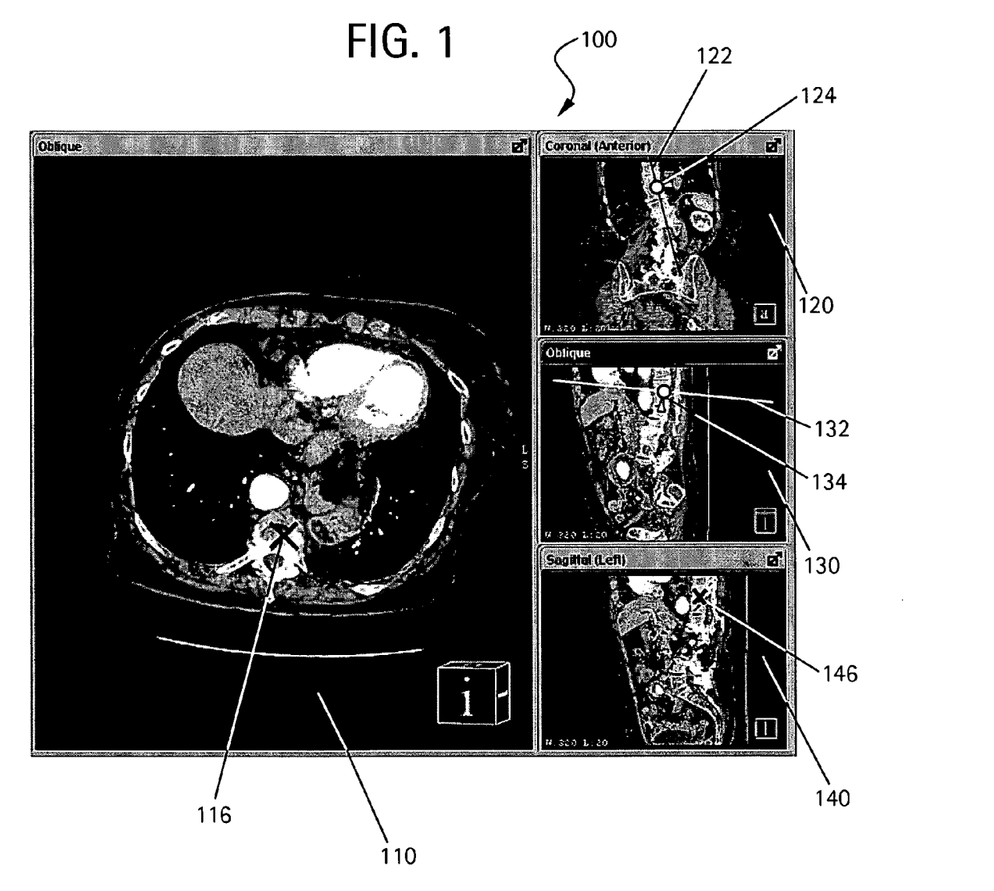
FIG. 1 illustrates a screenshot of multiple viewports according to an embodiment of the invention.

FIG. 1 illustrates a screenshot 100 of multiple viewports according to an embodiment of the invention. Screenshot 100 is a visual representation of the viewports displayed on device 610 when display routine 640 is implemented or carried out by device 610. For example, screenshot 100 may be a visual representation of computer software running on device 610. Screenshot 100 includes multiple viewports 110, 120, 130 and 140. While four viewports are illustrated in FIG. 1, any number of viewports may be used in accordance with the present invention. For example, two or more viewports may be used in accordance with embodiments of the present invention.

Each of viewports 110, 120, 130, 140 may include a 2D cross-sectional image of a 3D imaged object at a given angle of display. In an embodiment of the present invention, a user may select which 2D image is displayed in each viewport. In another embodiment of the present invention, the 2D image (s) displayed in each viewport is preset.

In an embodiment of the present invention, a 2D image displayed in first viewport 120 is displayed at a preset angle of display. In another embodiment of the present invention, the angle of display of a 2D image displayed in first viewport 120 can be free rotated to any position by a user of device 610. For example, a user may employ an input device connected to device 610 to free rotate the angle of display of a 2D image displayed in first viewport 120.

At least one technical effect of display routine 640 is to create a sufficient number of viewports to display all 2D images simultaneously. In other words, display routine 640 can be used to display a number of viewports sufficient to display all 2D images desired by a user of device 610.

In an embodiment of the present invention, the viewports created by display routine 640 may be provided in a sequence. In other words, viewport 120 may be the first viewport, viewport 130 may be the second viewport, viewport 140 may be the third viewport, and viewport 110 may be the final viewport, for example.

The angle of display or angle of cross-section for each 2D image or stack of images may be equivalent or differ in all viewports or in any subset of viewports. In an embodiment of the present invention, a user may select the angle of display and/or plane for each 2D image displayed in each viewport. In another embodiment of the present invention, the exact angle and/or plane at which the image is viewed in one or more viewports may be preset.

In an embodiment of the present invention, the angle of display or image plane of a 2D image displayed in one viewport is orthogonal to the angle of display or image plane of a 2D image displayed in a previous viewport. In another embodiment, the angle of display or image plane of a 2D image displayed in one viewport is orthogonal to the angle of display or image plane of a 2D image displayed in a previous viewport and to the angle of display or image plane of a 2D image displayed in a subsequent viewport.

In an embodiment of the present invention, a 2D image displayed in a viewport is centered at a control line of a 2D image displayed in a previous viewport.

As described above, each control viewport 120, 130, 140 may display a cross sectional view of a 3D volume. For example, in FIG. 1, viewport 120 may display a coronal (anterior) view of a 3D volume of a patient's spine. In addition, viewport 130 may display an oblique cross sectional view of the same 3D volume and viewport 140 may display a sagittal (left) cross sectional view of the same 3D image, for example. Another viewport (e.g., viewport 110) in screen shot 100 of FIG. 1 may display a final view of the 3D volume. Final viewport 110 may include another cross sectional image (such as another oblique cross sectional image of the 3D image) defined by the movement of control lines 122, 132 in control viewports 120, 130, as described in more detail below.

One or more viewports created by display routine 640 can include a control line. For example, viewports 120 and 130 of screenshot 100 each include control lines 122 and 132, respectively. A control line 122, 132 can represent a plane in which a view of the 3D image is presented in a subsequent control viewport and/or in final viewport 110. For example, control line 122 in first control viewport 120 may represent the 2D image plane of a 3D volume displayed in second control viewport 130 and control line 132 in second control viewport 130 may represent the 2D image plane of the 3D volume displayed in final viewport 110.

In an embodiment of the present invention, each viewport in a subset of the viewports displayed by display routine 640 includes a control line.

In an embodiment of the present invention, each viewport may include additional markings to help orient a user. For example, a viewport may include a directional marker 124, 134. Directional marker 124, 134 may represent the direction at which the 3D volume is presented in final viewport 110 as a 2D image. In other words, control line 122 in viewport 120 represents the 2D cross-section in which the 3D volume is presented in final viewport 110. Without directional marker 124 in viewport 120, it may be unclear the direction from which the image plane (defined by control line 122) is viewed. For example, without directional marker 124 pointing down and to the left of control viewport 120, it may be unclear whether the 2D image plane defined by control line 122 is being viewed from the right or the left as displayed in final viewport 110. However, with the inclusion of directional marker 124, it is clear that the 2D image in final viewport 110 represents a 2D image plane defined by control line 122 as viewed from the right side of control line 122.

In another example, directional marker 134 in viewport 130 may assist a user in determining that the image plane defined by control line 132 is being viewed (in final viewport 110) from the bottom of control line 132.

In an embodiment of the present invention, directional marker 124, 134 is represented by a triangle. However, in other embodiments, directional marker 124, 134 may be represented by any other symbol or marking that conveys the direction at which an image plane defined by a control line is viewed. For example, directional marker 124, 134 may be represented by an arrow or line.

Directional marker 124, 134 may also include a control line center point. The center point may represent a center point along a control line. In other words, directional marker 124 can include a circle, for example, indicating the center of control line 122. In another example, directional marker 134 can include a circle, for example, indicating the center of control line 132. While a circle is used for the center point in directional marker 124, 134, any point, line, or geometric object may be used to indicate the center point of a control line.

The center point of a control line may also be represented by a center point as represented by 116, 146 in FIG. 1. In other words, the "X" in final viewport 110 marked with 116 and the "X" in third control viewport 140 marked with 146 represent the center point of control lines. However, while an "X" is used as center points 116, 146, any point, line, or geometric object may be used in its place.

A user may employ an input device connected to or included in device 610 to move one or more control lines in one or more viewports. When a control line in one viewport is moved, an angle of display or angle of cross section of a 2D image or stack of images displayed in another viewport is accordingly modified or altered by modifying routine 650. In other words, in accordance with an embodiment of the present invention, at least one technical effect of modifying routine 650 is to modify or alter an angle of display or angle of cross-section of a 2D image or stack of cross-sectional images based on and simultaneous with the movement of a control line in another 2D image.

As described above, a control line in one viewport represents an image plane of at least one other 2D image displayed in at least one other viewport at a given angle of display. When the control line is moved, the image plane of the at least one other 2D image displayed in the at least one other viewport simultaneously changes.

As described above, at least one technical effect of modifying routine 650 is to cause device 610 to alter the angle of display or angle of cross-section of a 2D image or stack of images as a corresponding control line is moved. In other words, as a user moves control line 122 displayed in a first viewport 120, modifying routine 650 causes an angle of display or angle of cross-section of another 2D image in another viewport (such as second, third or final viewports 130, 140, 110) to make a corresponding change, at the same time that the control line is moved for example. By doing so, modifying routine 650 permits a user to witness the real time effects of moving a control line in one viewport on the angle of display or angle of cross-section of at least one other 2D image in at least one other viewport. Such a simultaneous change allows for the effects of moving a control line in one control viewport to be viewed in one or more subsequent viewports.

As understood by one of ordinary skill in the art, the terms and phrases "real time," "at the same time," and "simultaneous" do not exclude any small delay inherent in the processing of images and/or sets of instructions (e.g., display routine 640 and/or modifying routine 650) by a device 610. Instead, various embodiments of the present invention provide for the ability of a user to witness to effects of moving a control line in a first 2D image on other 2D images, all while viewing both the first and other 2D images. For example, a user viewing a first, second and final 2D images all at the same time may move a control line in the first and/or second images (multiple times and in any order), and witness the effects of moving the control line(s) on the display of the first and/or second and/or final 2D images all at the same time.

In an embodiment of the present invention, each of the viewports displayed by display routine 640 may be linked so that a control line in one viewport controls the angle of display or angle of cross-section in another 2D image or stack of images displayed in another viewport. For example, first viewport 120 may be linked to second viewport 130 and second viewport 130 may be linked to final viewport 110 so that movement of first control line 122 in first viewport 120 controls the angle of display of a 2D image displayed in second viewport 130, and movement of second control line 132 controls the angle of display of a 2D image displayed in final viewport 110.

In an embodiment of the present invention, modifying routine 650 alters an angle of display or angle of cross-section of all 2D images displayed in viewports subsequent to the viewport in which a control line is moved. In other words, if control line 122 in first control viewport 120 is moved, modifying routine 650 then alters the angle of display of the 2D image displayed in second control viewport 130, which consequently causes the angle of display of the 2D image displayed in third control viewport 140 to be altered by modifying routine 650, which then consequently causes the angle of display of the 2D image displayed in final viewport 110 to be altered by modifying routine 650, for example. The movement of a control line in one viewport in a sequence of viewports therefore causes a domino-like effect on the angle(s) of display in the 2D images displayed in all subsequent viewports.

In an embodiment of the present invention, modifying routine 650 is capable of modifying a plurality of angles of display in a plurality 2D images in any order selected by a user. For example, a user may first move control line 122 in first viewport 120, which causes modifying routine 650 to alter the angles of display of the 2D images displayed in second, third and final viewports 130, 140, 110. Next, the user may move control line 132 in second viewport 130, which then causes modifying routine 650 to alter the angles of display or angle of cross-section of the 2D images displayed in third and final viewports 140, 110, for example. Finally, the user may move control line 122 in first control viewport 120 again, thereby causing modifying routine 650 to alter the angles of display of the 2D images displayed in second, third and final viewports 130, 140, 110, for example. In this way, a user of system 600 may repeatedly move multiple control lines in multiple viewports in order to achieve a 2D image in a final viewport at a desired angle of display or angle of cross-section. In other words, the present invention provide a user with the ability to adjust two or more cross-sectional images or stacks of images at the same time without having to page back and forth between different image processing steps. Therefore, the present invention also minimizes the number of iterations required to correctly view desired anatomy in a 2D cross-sectional image.

Figure 4:
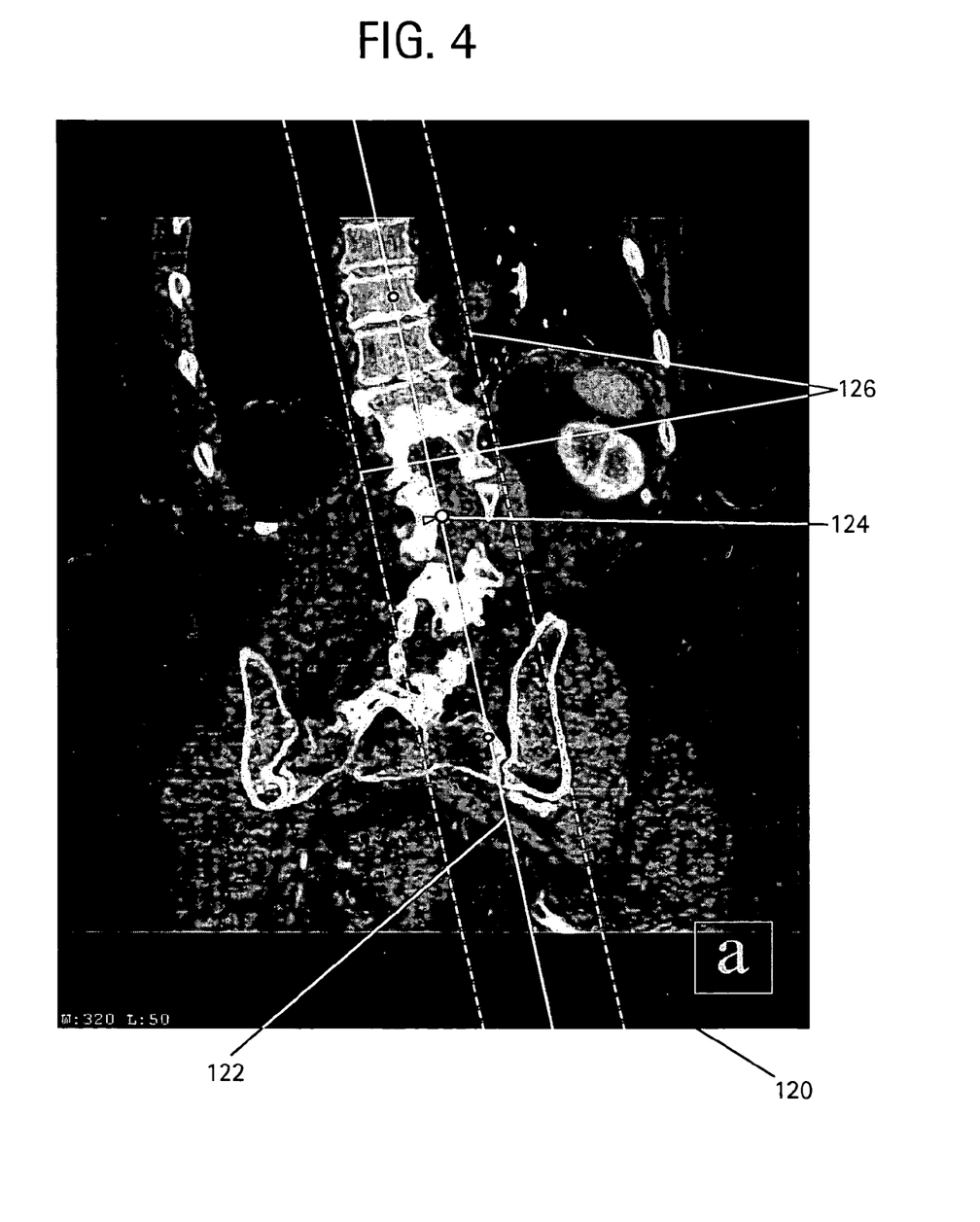
FIG. 4 illustrates first control viewport with additional control markings in accordance with an embodiment of the present invention.

In an embodiment of the present invention, one or more control lines In one or more viewports may include additional markings or controls. FIG. 4 illustrates first control viewport 120 with additional control markings 126 in accordance with an embodiment of the present invention. In accordance with an embodiment of the present invention, at least one technical effect of display routine 640 is to display a control line such as line 122 along with one or more markings such as the dashed lines of control markings 126 (for example) shown in FIG. 4 to represent slice thickness. Slice thickness relates to how "thick" a 2D image is. For example, a user can prescribe how thick a 2D image is; it is as if the user stacked a number of 2D images on top of each other and the display of the final 2D image is a combination of the images. There are several ways to combine the pixels. For example, each pixel in the final 2D image can be the highest value pixel in the stack of 2D images. In another example, each pixel in the final 2D image can be an average of all the pixels in the stack of 2D images. The stack of 2D images is referred to as a "slab." Slice thickness refers to the thickness of this slab. For medical images slice thickness can be measured in mm. That is, slice thickness can be measured in real-world space.

While dashed lines are used in FIG. 4 as additional control markings 126, any geometric shape or object may be used to indicate a slice thickness in accordance with an embodiment of the present invention. In addition, while markings 126 are shown as displayed in first control viewport 120 in FIG. 4, markings 126 may be displayed in any one or more viewports displayed by display routine 640.

In an embodiment of the present invention, the slice thickness indicated by markings 126 may be adjusted by a user of device 610. For example, a user may employ an input device connected to device 610 to adjust the slice thickness of a 2D image by moving markings 126.

Figure 6:
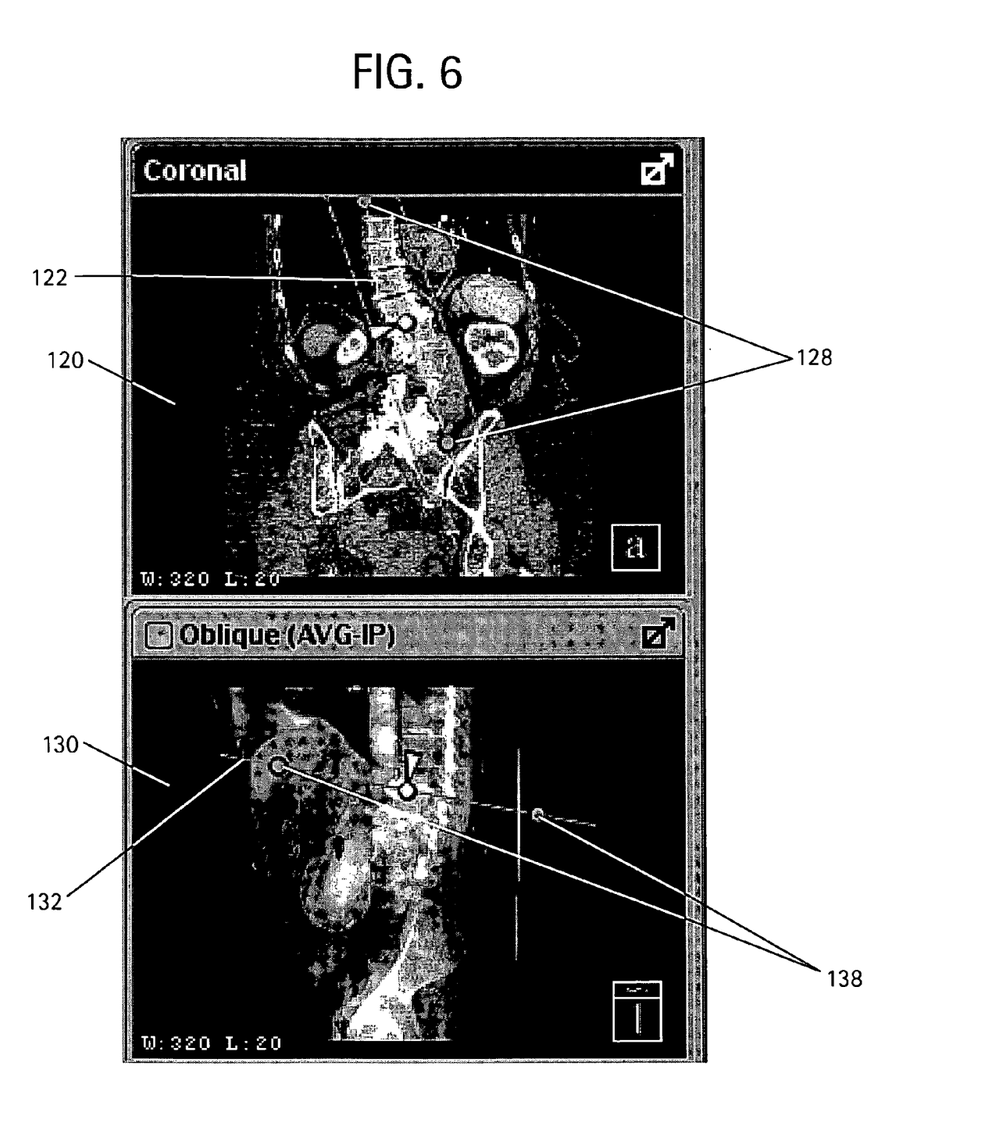
FIG. 6 illustrates first and second control viewports with additional rotational control markings in accordance with an embodiment of the present invention.

In an embodiment of the present invention, one or more control lines in one or more viewports may include additional markings or controls to aid in the movement of a control line. FIG. 6 illustrates first and second control viewports 120, 130 with additional rotational control markings 128, 138 in accordance with an embodiment of the present invention. In accordance with an embodiment of the present invention, at least one technical effect of display routine 640 is to display rotational control markings 128, 138 on one or more ends of control lines 122, 132 as shown in FIG. 6. Rotational control markings 128, 138 can be used to aid a user in rotating a control line. For example, a user may employ an input device, such as a mouse or stylus, to click or select one of control markings 128, 138. Once a control marking 128, 138 is selected, the user may move the input device and cause the corresponding control line to rotate. While circles are used in FIG. 6 as rotational control markings 128, 138, any geometric shape or object may be used in accordance with an embodiment of the present invention. In addition, while markings 128, 138 are shown as displayed in first and second control viewports 120, 130 along with control lines 122, 132 in FIG. 6, markings 128, 138 may be displayed in any one or more viewports displayed by display routine 640 along with any control line.

Figure 2:
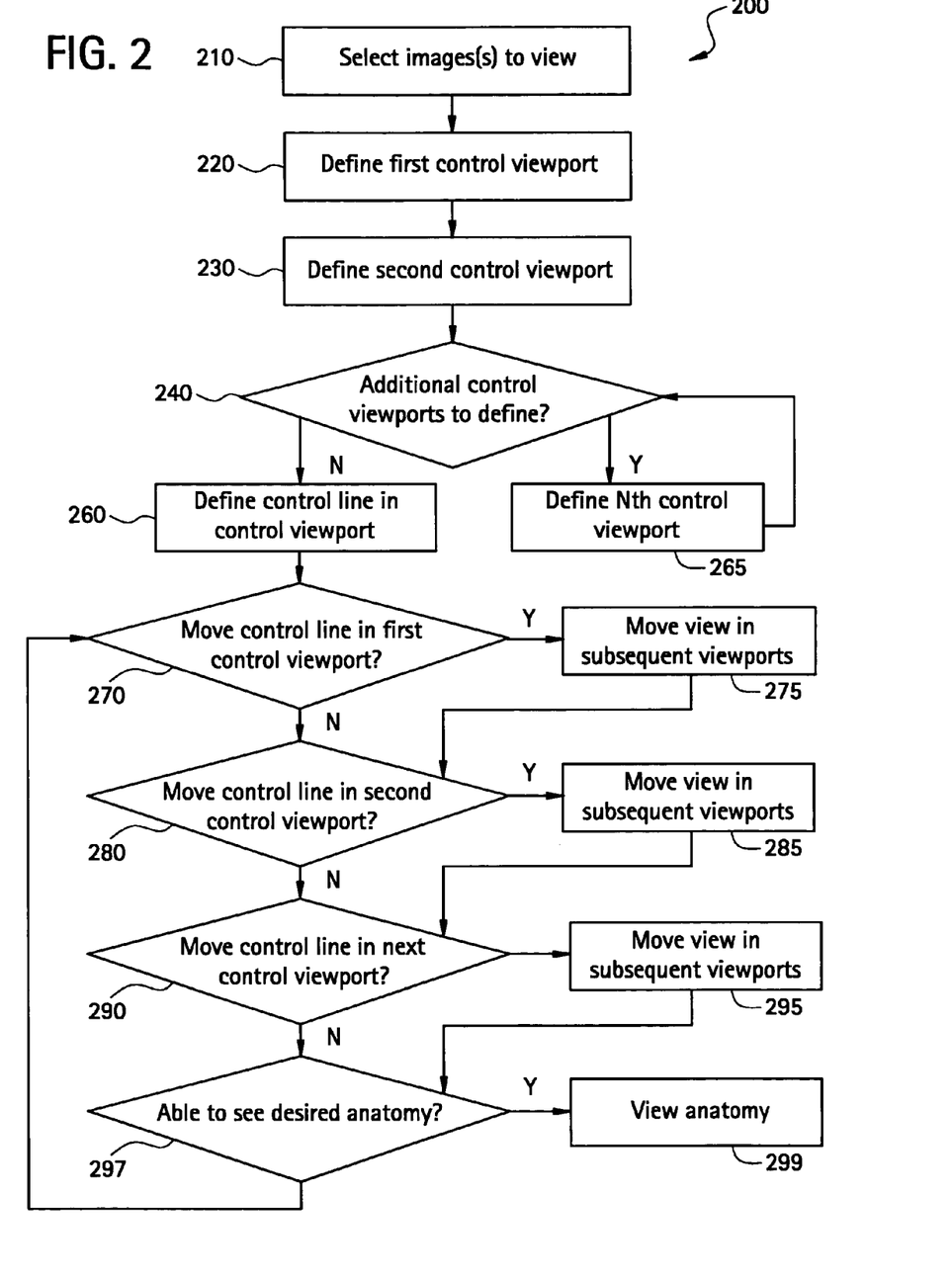
FIG. 2 illustrates a flowchart for a method to define the 3D oblique cross-section of anatomy at a specific angle and be able to easily modify multiple angles of display simultaneously in accordance with an embodiment of the present invention.

FIG. 2 illustrates a flowchart for a method 200 to define the 3D oblique cross-section of anatomy at a specific angle and be able to easily modify multiple angles of display simultaneously in accordance with an embodiment of the present invention. Method 200 may be used in conjunction with screenshot 100 of FIG. 100 in an embodiment of the present invention.

First, at step 210, one or more images are selected to be viewed on a display of a workstation or computer. Next, at step 220, a first control viewport 120 is selected or defined. First control viewport 120 includes a cross-sectional view of a 3D image, such as a 2D cross-sectional image or stack of images. A user may select the exact angle and/or plane at which the image is viewed in first control viewport 120. In another embodiment, the exact angle and/or plane at which the image is viewed in viewport 120 may be preset.

Next, at step 230, a second control viewport 130 is selected or defined. Second control viewport 130 includes a second cross sectional view of the 3D image. A user may select the exact angle and/or plane at which the image is viewed in second control viewport 130. In another embodiment, the exact angle and/or plane at which the image is viewed in second control viewport 130 may be preset.

Next, at step 240, a determination is made as to whether additional control viewports are selected or defined. If additional control viewports are to be selected or defined, then method 200 proceeds to step 265 and an additional control viewport is selected or defined. The additional control viewport can include, for example, third control viewport 140. Third control viewport 140 includes a third cross sectional view of the 3D volume. A user may select the exact angle and/or plane at which the image is viewed in third control viewport 140. In another embodiment, the exact angle and/or plane at which the image is viewed in third control viewport 140 may be preset.

As described above, each control viewport 120, 130, 140 may display a cross sectional view of a 3D volume. For example, control viewport 120 may display a coronal (anterior) view of a 3D volume of a patient's spine. In addition, control viewport 130 may display an oblique cross sectional view of the same 3D volume and control viewport 140 may display a sagittal (left) cross sectional view of the same 3D volume, for example. Another viewport (e.g., final viewport 110) in screen shot 100 of FIG. 1 may display a final view of the 3D volume. Final viewport 110 may include another cross sectional image (such as another oblique cross sectional image of the 3D volume) defined by the movement of control lines 122, 132 in control viewports 120, 130.

After the additional, or Nth, control viewport is defined or selected at step 265, method 200 proceeds to step 240 where another determination is made as to whether an additional control viewport is to be selected or defined. In this way, method 200 proceeds in a loop between steps 240 and 265 until all Nth control viewports are defined or selected. Once the total number of control viewports have been defined or selected, method 200 proceeds from step 240 to step 260. A user may select the total number of control viewports. In another embodiment, the total number of control viewports may be preset.

At step 260, a control line 122, 132 is defined or selected in one or more of the control viewports. For example, control line 122 may be selected or defined in control viewport 120 and/or control line 132 may be selected or defined in control viewport 130 of FIG. 1. A control line 122, 132 can represent a cross-sectional plane in which a view of the 3D volume is presented in a subsequent control viewport and/or in final viewport 110. For example, control line 122 in first control viewport 120 may represent the 2D image plane or cross-section of a 3D volume displayed in second control viewport 130; control line 132 in second control viewport 130 may represent the 2D image plane or cross-section of the 3D volume displayed in final viewport 110.

Next, at step 270, a determination is made as to whether a control line 122 in a first control viewport 120 is moving or has been moved. If control line 122 is moving or has been moved (for example, by a user selecting the line 122 with an input device such as a mouse or stylus and moving line 122 in viewport 120), method 200 proceeds to step 275.

At step 275, the control line and 2D view of the 3D volume displayed in subsequent control viewports and the final viewport is moved based on the movement of the control line in the first viewport. For example, as control line 122 in first control viewport 120 is moved, the cross-sectional plane defined by control line 122 changes. Therefore, as control line 122 moves, the 2D image or stack of images displayed in second control viewport 130 makes a corresponding change. In addition, the 2D images displayed in subsequent viewports (for example, second and third control viewports 130, 140 and final viewport 110) and/or control lines 132, 142 in subsequent viewports 130, 140 may also make a corresponding change. Such a simultaneous change allows for the effects of moving a control line in one control viewport to be viewed in one or more subsequent viewports. After step 275, method 200 proceeds to step 280.

If a determination is made that control line 122 in first control viewport 120 is not or was not moved, then method 200 proceeds to step 280.

At step 280, a determination is made as to whether control line 132 in second control viewport 130 is moving or has been moved. If control line 132 is moving or has been moved (for example, by a user selecting the line 132 with an input device such as a mouse or stylus and moving line 132 in viewport 130), method 200 proceeds to step 285.

At step 285, the 2D view of the 3D volume displayed in subsequent control viewports and/or the final viewport is moved based on the movement of the control line in the second viewport. For example, as control line 132 in second control viewport 130 is moved, the cross-sectional plane defined by control line 132 changes. Therefore, as control line 132 in second control viewport 130 moves, the 2D image displayed in subsequent control viewports (e.g., third control viewport 140) and/or in final viewport 110 makes a corresponding change. In addition, control lines in subsequent viewports (e.g., control line 142 in third control viewport 140) may also make corresponding changes. In other words, any movement of control line 132 in second control viewport 130 does not affect the image or control line 122 displayed in the previous first control viewport 120. Any control line 132 movement only affects the display of images in subsequent control viewports and in final viewport 110. After step 285, method 200 proceeds to step 290.

If a determination is made at step 280 that control line 132 in second control viewport 130 is not or was not moved, then method 200 proceeds to step 290.

At step 290, a determination is made as to whether a control line in the next control viewport is moving or has been moved.

If a control line in the next control viewport is moving or has been moved (for example, by a user selecting the line 142 in third control viewport 140 with an input device such as a mouse or stylus and moving line 142 in viewport 140), method 200 proceeds to step 295.

At step 295, the 2D image or stack of images of the 3D volume displayed in subsequent control viewports and/or the final viewport is moved based on the movement of the control line in the previous control viewport. In addition, control lines in subsequent control viewports are also moved based on the movement of the control line in the previous control viewport. For example, as control line 142 in third control viewport 140 is moved, the cross-section defined by control line 142 changes. Therefore, as the cross-section or 2D image plane changes in third control viewport 140 (again, as defined by control line 142), the 2D image displayed in subsequent control viewports and in final viewport 110 makes a corresponding change. In addition, the control lines displayed in subsequent control viewports also make a corresponding change. In other words, any movement of control line 142 in third control viewport 140 does not affect the image or control lines 122, 132 displayed in the previous first and second control viewports 120, 130. Any control line 142 movement only affects the display of images and control lines in subsequent control viewports and in final viewport 110.

After step 290 and/or step 295, method 200 proceeds to step 297 where a determination is made if a user is able to see desired anatomy correctly based on the previous movement of one or more control lines. If the desired anatomy is able to be correctly viewed according to a user's wishes, method 200 proceeds to step 299 where the user views the anatomy. If the desired anatomy is not able to be correctly viewed, method 200 proceeds back to step 270, where one or more of the control lines may be moved in order to properly position the anatomy for the user.

Steps 270 through 297 continue in a loop until the desired anatomy is positioned in a manner preferential to a user (that is, until the desired anatomy is able to be viewed).

In an embodiment, method 200 may proceed from any one or more of steps 280, 285, 290 and 295 to steps 270, 280, or 290. In addition, method 200 may proceed from any one or more of steps 290 and 295 to step 280. In other words, method 200 may proceed by determining whether a control line has been moved or is moved in a subsequent control viewport (e.g., at step 280 or 290, and then changing the view in all viewports subsequent to that control viewport at step 285 or 295, respectively) and then determining whether a control line in a previous viewport control has been moved or is being moved (e.g., by proceeding back to step 270 or 280). For example, a control line in an (N−1) control viewport may be moved, thereby causing the views in all subsequent control viewports (e.g., the Nth viewport and the final viewport) to change, as described above. Next, a control line in a previous control viewport (e.g., an (N−2), (N−3), (N−4) and so on control viewport) may be moved, thereby causing the views in all subsequent viewports to change, as described above.

Figure 3:
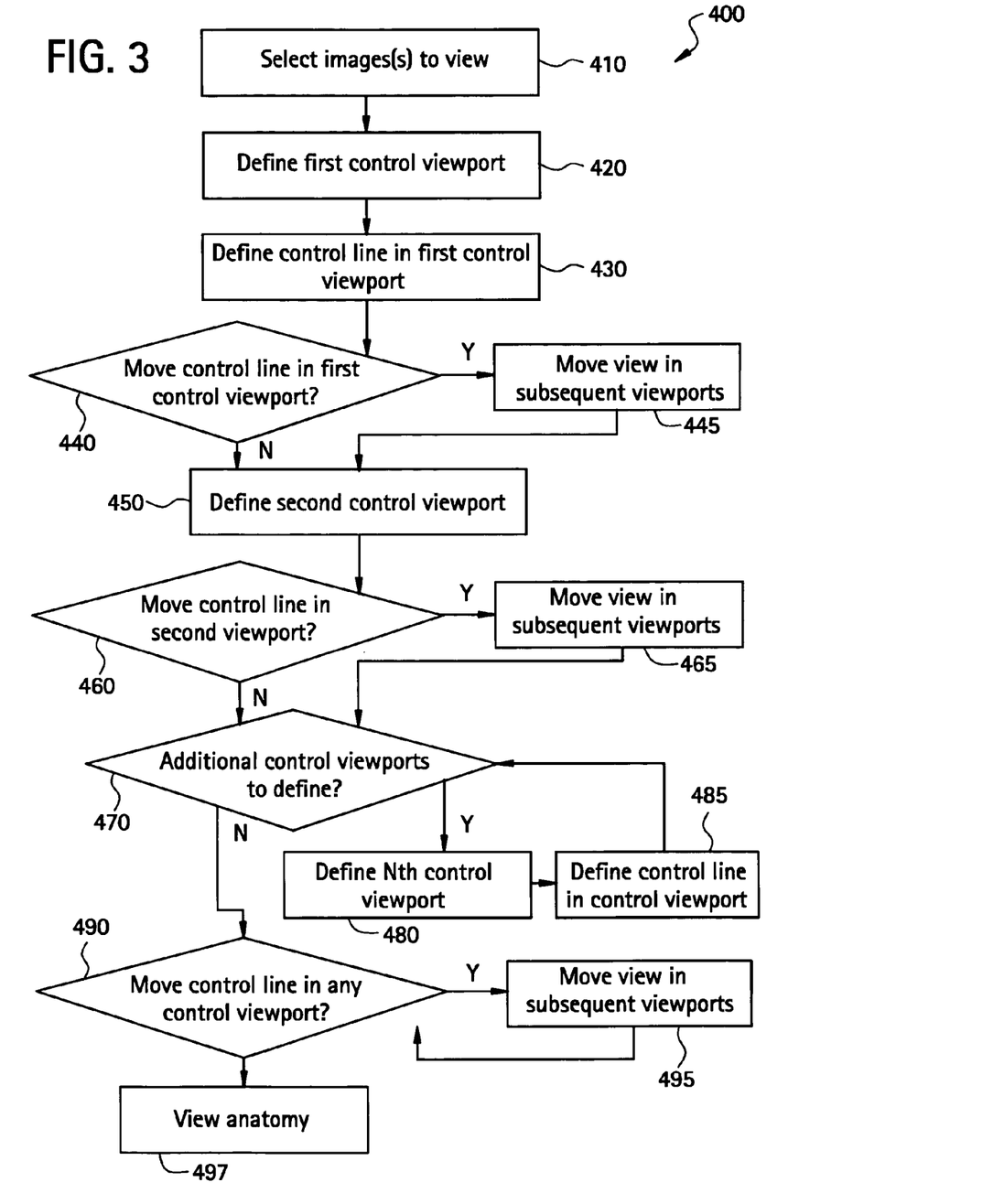
FIG. 3 illustrates a flowchart for a method to define the 3D oblique cross-section of anatomy at a specific angle and be able to easily modify multiple angles of display simultaneously in accordance with another embodiment of the present invention.

FIG. 3 illustrates a flowchart for a method 400 to define the 3D oblique cross-section of anatomy at a specific angle and be able to easily modify multiple angles of display simultaneously in accordance with another embodiment of the present invention. Method 400 may be used in conjunction with screenshot 100 of FIG. 100 in an embodiment of the present invention.

First, at step 410, one or more images are selected to be viewed on a display of a workstation or computer, as described above. Next, at step 420, a first control viewport 120 is selected or defined, as described above. First control viewport 120 includes a cross-sectional view of a 3D volume. A user may select the exact angle and/or plane at which the image is viewed in first control viewport 120. In another embodiment, the exact angle and/or cross-sectional plane at which the image or stack of images is viewed in first control viewport 120 may be preset.

At step 430, a control line 122 is defined or selected in first control viewport 120, as described above. For example, control line 122 may be selected or defined in control viewport 120 and/or control line 132 may be selected or defined in control viewport 130 of FIG. 1.

Next, at step 440, a determination is made as to whether a control line 122 in first control viewport 120 is moving or has been moved, as described above. If control line 122 is moving or has been moved (for example, by a user selecting the line 122 with an input device such as a mouse or stylus and moving line 122 in viewport 120), method 400 proceeds to step 445.

At step 445, the control line and cross-sectional image or stack of images of the 3D volume displayed in subsequent control viewports and the final viewport is moved based on the movement of the control line in the first viewport, as described above. For example, as control line 122 in first control viewport 120 is moved, the cross-sectional plane defined by control line 122 changes. Therefore, as the cross-sectional plane changes in first control viewport 120 (again, as defined by control line 122), the cross-sectional image or stack of images displayed in subsequent control viewports (e.g., second and third control viewports 130, 140) and in final viewport 110 makes a corresponding change. In addition, any control lines 132, 142 in subsequent viewports 130, 140 may also make a corresponding change. After step 445, method 400 proceeds to step 450.

If a determination is made at step 440 that control line 122 in first control viewport 120 is not or was not moved, then method 400 proceeds to step 450.

At step 450, a second control viewport 130 is selected or defined, as described above. Second control viewport 130 includes a second cross sectional image or stack of images of the 3D volume. A user may select the exact angle and/or cross-sectional plane at which the image or stack of images is viewed in second control viewport 130. In another embodiment, the exact angle and/or cross-sectional plane at which the image is viewed in second control viewport 130 may be preset.

At step 460, a determination is made as to whether control line 132 in second control viewport 130 is moving or has been moved, as described above. If control line 132 is moving or has been moved (for example, by a user selecting the line 132 with an input device such as a mouse or stylus and moving line 132 in viewport 130), method 400 proceeds to step 465.

At step 465, the cross-sectional image or stack of images of the 3D volume displayed in subsequent control viewports and the final viewport is moved based on the movement of the control line in the second viewport, as described above. For example, as control line 132 in second control viewport 130 is moved, the angle of display or angle of cross-section of the cross-sectional image or stack of images defined by control line 132 changes. Therefore, as the cross-sectional plane changes in second control viewport 130 (again, as defined by control line 132), the 2D image or stack of images displayed in subsequent control viewports (e.g., third control viewport 140) and in final viewport 110 makes a corresponding change. In addition, control lines in subsequent viewports (e.g., control line 142 in third control viewport 140) may also make corresponding changes. In other words, any movement of control line 132 in second control viewport 130 does not affect the image or control line 122 displayed in the previous first control viewport 120. Any control line 132 movement only affects the display of images in subsequent control viewports 140 and in final viewport 110. After step 465, method 400 proceeds to step 470.

If a determination is made at step 460 that control line 132 in second control viewport 130 is not or was not moved, then method 400 proceeds to step 470.

Next, at step 470, a determination is made as to whether additional control viewports are selected or defined, as described above. If additional control viewports are to be selected or defined, then method 400 proceeds to step 480 and an additional control viewport is selected or defined, as described above. The additional control viewport can include, for example, third control viewport 140. Third control viewport 140 includes a third cross sectional image or stack of images of the 3D volume. A user may select the exact angle and/or cross-sectional plane at which the image or stack of images is viewed in third control viewport 140. In another embodiment, the exact angle and/or cross-sectional plane at which the image or stack of images is viewed in third control viewport 140 may be preset.

After the additional, or Nth, control viewport is defined or selected at step 480, method 400 proceeds to step 485 where a control line is defined or selected in the additional control viewport defined or selected at step 480, as described above. From step 485, method 400 proceeds back to step 470 where another determination is made as to whether an additional control viewport is to be selected or defined, as described above. In this way, method 400 proceeds in a loop between steps 470, 480 and 485 and 485 until all Nth control viewports are defined or selected. Once the total number of control viewports have been defined or selected, method 400 proceeds from step 470 to step 490. A user may select the total number of control viewports. In another embodiment, the total number of control viewports may be preset.

At step 490, a determination is made as to whether a control line in any control viewport is moving or has been moved, as described above. If a control line in the next control viewport is moving or has been moved (for example, by a user selecting the line 142 in third control viewport 140 with an input device such as a mouse or stylus and moving line 142 in viewport 140), method 400 proceeds to step 495.

At step 495, the cross-sectional image or stack of images of the 3D volume displayed in subsequent control viewports and the final viewport is moved based on the movement of the control line in the previous control viewport, as described above. In addition, control lines in subsequent control viewports may also be moved based on the movement of the control line in the previous control viewport. For example, as control line 142 in third control viewport 140 is moved, the cross-sectional plane defined by control line 142 changes. Therefore, as the cross-sectional plane changes in third control viewport 140 (again, as defined by control line 142), the 2D image or stack of images displayed in subsequent control viewports and in final viewport 110 makes a corresponding change. In addition, the control lines displayed in subsequent control viewports also make a corresponding change. In other words, any movement of control line 142 in third control viewport 140 does not affect the image or control lines 122, 132 displayed in the previous first and second control viewports 120, 130. Any control line 142 movement only affects the display of images and control lines in subsequent control viewports and in final viewport 110.

If it is determined at step 490 that no control lines in any of the control viewports have been moved, method 400 proceeds to step 497 where a user views the anatomy.

Steps 490 and 495 continue in a loop until all control viewports defined or selected in steps 470 and 480 have been examined to determine whether a control line in each viewport has been moved. For example, a user may first move a control line in a first control viewport, followed by moving a control line in a second control viewport, followed by an additional movement of the control line in the first control viewport.

This invention minimizes the number of iterations required to visualize specific anatomy by visualizing the multiple steps, at the same time.

Current solutions to this problem require a multiple-step approach that often times call for multiple iterations. Adjusting the first angle, and then going to a second page to adjust the second, and so on. If, while adjusting the second angle, the user decides they need to further adjust the first angle, they need to go back to the original image, and can no longer see the second oblique angle. This invention allows the user to see the original image, the first oblique and the second oblique, (and even a third oblique if desired), and adjust each while viewing the others.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features that come within the spirit and scope of the invention.

What is claimed is:

1. A method to modify one or more angles of cross-section in one or more cross-sectional images of a three-dimensional ("3D") volume simultaneously, said method including:
    providing a plurality of viewports each configured to display a two-dimensional ("2D") image, each said 2D image representative of a cross-section of said 3D volume, wherein the plurality of viewports includes a first viewport, a second viewport and a third viewport;
    moving a control line in the first viewport;
    simultaneous with moving the control line in the first viewport, altering an angle of the 2D image displayed in the second viewport;
    moving a control line in the second viewport: and
    simultaneous with moving the control line in the second viewport, altering an angle of the 2D image displayed in the third viewport and not altering an angle of the 2D image displayed in the first viewport.

2. The method of claim 1, wherein the control line in the first viewport represents a cross-sectional plane of said 3D volume, the plane corresponding with the 2D image displayed in the second viewport.

3. The method of claim 1, wherein said 2D images displayed in said viewports are capable of being viewed simultaneously.

4. The method of claim 1, wherein the control line in the second viewport represents a cross-sectional plane of said 3D volume, the plane corresponding with the 2D image displayed in the third viewport.

5. The method of claim 1, wherein altering the angle of the 2D image displayed in the second viewport includes altering the position of the control line in the second viewport.

6. The method of claim 1, wherein at least one of said control lines includes an indication of a slice thickness.

7. A computer-readable storage medium encoded with a set of instructions for a computer, said instructions including:
    a display routine configured to display a plurality of two-dimensional ("2D") images representative of cross-sections of a three-dimensional ("3D") volume in a plurality of viewports, wherein the plurality of viewports includes a first viewport, a second viewport and a third viewport each configured to display one of the 2D images; and an angle of cross-section modifying routine configured to :

(1) alter an angle of the 2D image displayed in the second viewport based on and simultaneous with a movement of a control line in the first viewport, (2) alter an angle of the 2D image displayed in the third viewport based on and simultaneous with a movement of a control line in the second viewport, and (3) not alter an angle of the 2D image displayed in the first viewport based on the movement of the control line in the second viewport.

8. The set of instructions of claim 7, wherein the control line in the first viewport represents a cross-sectional plane of said 3D volume, the plane corresponding with the 2D image displayed in the second viewport.

9. The set of instructions of claim 7, wherein said display routine is configured to display said 2D images simultaneously.

10. The set of instructions of claim 7, wherein the control line in the second viewport represents a cross-sectional plane of said 3D volume, the plane corresponding with the 2D image displayed in the third viewport.

11. The set of instructions of claim 7, wherein altering the angle of the 2D image displayed in the second viewport includes altering the position of the control line in the second viewport.

12. The set of instructions of claim 7, wherein at least one of said control lines includes an indication of a slice thickness.

13. A method for adjusting an angle of cross-section in at least one of a plurality of two-dimensional ("2D") images, said method including:

providing a plurality of viewports including a first viewport configured to display a first 2D image, a second viewport configured to display a second 2D image and a third viewport configured to display a third 2D image, said first, second and third 2D images each representative of one or more cross-sections of a three-dimensional ("3D") volume;

displaying a plurality of control lines including a first control line displayed in said first viewport and a second control line displayed in said second viewport, said first control line configured to represent a cross-sectional plane of said second 2D image at a first angle of cross-section and said second control line configured to represent a cross-sectional plane of said third 2D image at a second angle of cross-section;

moving said first control line;

simultaneous with moving said first control line, adjusting said first angle of cross-section of said second 2D image and said second angle of cross-section of said third 2D image;

moving said second control line; and simultaneous with moving said second control line, adjusting said second angle of cross-section of said third 2D image and not adjusting an angle of display of said first 2D image.

14. The method of claim 13, wherein said step of moving said second control line occurs prior to said step of moving said first control line.

15. The method of claim 13, wherein each of said first, second and third viewports and said first, second and third 2D images are capable of being viewed simultaneously during said moving steps.

* * * * *